United States Patent [19]

Ou et al.

[11] Patent Number: 5,907,076
[45] Date of Patent: *May 25, 1999

[54] PROCESS FOR SELECTIVELY SEPARATING HYDROGEN, OR BOTH HYDROGEN AND CARBON MONOXIDE FROM OLEFINIC HYDROCARBONS

[75] Inventors: Di-Yi Ou, Houston; Stephen Neil Vaughn, Kingwood; Lawrence Gilbert Daniel, Crosby, all of Tex.

[73] Assignee: Exxon Chemical Patents Inc., Houston, Tex.

[21] Appl. No.: 08/880,611

[22] Filed: Jun. 23, 1997

Related U.S. Application Data

[60] Provisional application No. 60/033,950, Dec. 31, 1996.
[51] Int. Cl.⁶ ....................................................... C07C 7/00
[52] U.S. Cl. ........................ 585/800; 585/802; 585/809; 423/247; 423/248; 423/655
[58] Field of Search .................................... 423/248, 247, 423/655, 656; 585/800, 802, 843, 850, 855, 809

[56] References Cited

U.S. PATENT DOCUMENTS

| | | | |
|---|---|---|---|
| 1,911,780 | 5/1933 | White et al. | 423/248 |
| 3,549,719 | 12/1970 | Duyverman et al. | 423/248 |
| 3,615,217 | 10/1971 | O'Brien et al. | 23/213 |
| 4,185,039 | 1/1980 | Eden | 260/654 A |
| 4,299,800 | 11/1981 | Nishikawa et al. | 423/219 |
| 4,435,607 | 3/1984 | Imai | 585/443 |
| 4,604,275 | 8/1986 | Murib | 423/437 |
| 4,652,687 | 3/1987 | Imai et al. | 585/319 |
| 4,788,371 | 11/1988 | Imai et al. | 585/443 |
| 4,914,075 | 4/1990 | Bricker et al. | 502/330 |
| 5,045,297 | 9/1991 | Bonifaz et al. | 423/437 R |
| 5,124,500 | 6/1992 | Clark et al. | 585/655 |
| 5,157,204 | 10/1992 | Brown et al. | 585/850 |
| 5,625,116 | 4/1997 | Flammini et al. | 585/848 |

FOREIGN PATENT DOCUMENTS

| | | |
|---|---|---|
| 1 231 071 | 9/1960 | France . |
| 12 98 985 | 7/1969 | Germany . |
| 690 718 | 4/1953 | United Kingdom . |
| 1 063 420 | 3/1967 | United Kingdom . |
| 1 324 826 | 7/1973 | United Kingdom . |

OTHER PUBLICATIONS

PCT International Search Report (International application No. PCT/US97/23875).

*Primary Examiner*—Gary P. Straub
*Assistant Examiner*—Timothy C. Vanoy
*Attorney, Agent, or Firm*—Bradley A. Keller

[57] ABSTRACT

A process is disclosed for the separation and removal of hydrogen, alone or together with carbon monoxide, from a mixture of these gases with olefinic hydrocarbons by contacting the mixture with oxygen over a catalyst at conditions sufficient to oxidize the hydrogen to form water while suppressing reaction of the reactive, unsaturated hydrocarbons. The catalyst contains at least one metal or metal oxide from Groups Ib, IIb, IIIa, IVa and Va of the Periodic Table, and the temperature of the reaction may range from about 40° C. to 300° C. and a pressure of about 14.7 psig to 1,000 psig, and the flow rate of the entering feed ranges from about 1 GHSV to about 50,000 GHSV. The process can be conducted using one, two or three reaction zones.

19 Claims, No Drawings

PROCESS FOR SELECTIVELY SEPARATING HYDROGEN, OR BOTH HYDROGEN AND CARBON MONOXIDE FROM OLEFINIC HYDROCARBONS

This application claims priority to U.S. Provisional Patent Application No. 60/033,950, filed Dec. 31, 1996.

FIELD OF THE INVENTION

This invention relates to a process for chemically separating hydrogen, or hydrogen and carbon monoxide, from hydrocarbons containing reactive unsaturates, such as olefins and aromatics. In particular, it relates to a process for the reactive separation of hydrogen and carbon monoxide from olefinic and aromatic hydrocarbons by selective oxidation of the hydrogen and carbon monoxide, with minimal reaction of the olefins and aromatics.

BACKGROUND

The separation of hydrogen and carbon monoxide from mixtures containing reactive unsaturates, such as olefinic and or aromatic hydrocarbons, or mixtures containing light olefinic hydrocarbons such as ethylene, propylene, or other $C_2$–$C_4$ olefins, is a costly, but often necessary, operation because hydrogen and carbon monoxide are contaminants, or poisons for many downstream processes, such as polyethylene and polypropylene manufacturing.

The existing technology for separating hydrogen and carbon monoxide from reactive unsaturated hydrocarbons calls for cryogenic distillation which requires expensive equipment and high energy consumption. Other techniques, such as membrane, and absorption and adsorption are used only for separation of hydrogen from other components, and these techniques are effective only when the system pressure is high; generally greater than 100 psi.

The reason that hydrogen and carbon monoxide are so difficult to separate from mixtures containing light olefins is that the physical properties of the contaminants, hydrogen and carbon monoxide, are very similar to the light olefins in the mixture that they are to be separated from.

For example, carbon monoxide and ethylene, are similar in terms of molecular dimension and bonding characteristics; which makes physical separation very difficult.

Accordingly, there exists a need for an improved process for the selective separation of hydrogen and carbon monoxide from mixtures of these gases with reactive unsaturated hydrocarbons, such as light olefinic hydrocarbons, without significant loss of the valuable olefins via side reactions.

SUMMARY OF THE INVENTION

The invention provides a process for removing hydrogen from a mixture which includes hydrogen and reactive unsaturated hydrocarbons which comprises contacting said mixture with oxygen or an oxygen-containing gas over a catalyst at reaction conditions sufficient to oxidize the hydrogen component of the mixture to form water while suppressing hydrogenation of the reactive unsaturated hydrocarbons of the mixture, and recovering an effluent rich in reactive unsaturated hydrocarbons therefrom.

Another embodiment provides a process for removing hydrogen and carbon monoxide from a mixture which includes hydrogen, carbon monoxide, and reactive saturated hydrocarbons which further comprises contacting said effluent, in a second reaction zone, over an oxidation catalyst, in the presence of oxygen or an oxygen-containing gas at conditions sufficient to oxidize the carbon monoxide component of the mixture to form carbon dioxide, and recovering from said second reaction zone an effluent which is rich in reactive saturated hydrocarbons, denuded of hydrogen and carbon monoxide.

Yet another embodiment provides a process for removing hydrogen and carbon monoxide from a mixture which includes hydrogen, carbon monoxide, and reactive saturated hydrocarbons which further comprises wherein the effluent from the second reaction zone is contacted in a third reaction zone with a water gas shift and hydrogenation catalyst to convert residual amounts of hydrogen and carbon monoxide to water.

DETAILED DESCRIPTION

The present invention, which satisfies this need and others, relates to a process for the separation, and removal, of hydrogen, or both hydrogen and carbon monoxide from a mixture which includes hydrogen, or both hydrogen and carbon monoxide, and reactive unsaturated hydrocarbons. The reactive unsaturated hydrocarbons include olefinic compounds such as ethylene, propylene, butylenes, or the like; paraffinic or cyclic compounds such as methane, ethane, propane, butanes, cyclohexane, or the like; and aromatic compounds such as benzene, toluene, xylenes, or the like. The process may be operated in either gas phase or liquid phase. In one of its aspects, a mixture comprised of hydrogen and a light olefinic hydrocarbon, or light olefinic hydrocarbons, is contacted with oxygen or an oxygen-containing gas, e.g., air, over a catalyst highly selective to hydrogen oxidation at reaction conditions sufficient to oxidize the hydrogen component of the mixture to form water, while suppressing reaction of the light olefinic hydrocarbons of the mixture. It is important that the hydrogen-oxidation selective catalyst has no or minimum activity for hydrogenation of olefins. Depending on the quantity of oxygen injection, essentially either all of the hydrogen is consumed in the reaction zone, with some oxygen and little if any hydrogen passing downstream of the reaction zone; or all of the oxygen is consumed in the reaction zone, with some hydrogen and little if any oxygen passing down stream of the reaction zone.

In another aspect, a mixture comprised of hydrogen, carbon monoxide and a reactive unsaturated hydrocarbon, or a mixture of one or more of such hydrocarbons is contacted in an initial, or first reaction zone of a series, with oxygen or an oxygen-containing gas over a catalyst selective for hydrogen oxidation at conditions sufficient to oxidize the hydrogen component of the mixture to form water, while suppressing hydrogenation of the olefinic components of the mixture to obtain effluent which is fed to a second reaction zone of the series. In conducting this series of reactions it is essential to remove the hydrogen first to minimize, avoid, or suppress the hydrogenation reaction between the hydrogen and the reactive unsaturated hydrocarbons. In the second reaction zone, the effluent is contacted and reacted over an oxidation catalyst capable of oxidizing carbon monoxide in the presence of oxygen at conditions sufficient to oxidize the carbon monoxide component of the mixture to form carbon dioxide. The fact that most carbon-monoxide oxidation catalysts also promote olefin hydrogenation makes it critical to react essentially all or most of the hydrogen in the feed stream prior to its entering the second reaction zone. Suppression of the hydrogenation reaction is enhanced because of the relatively high concentration of carbon monoxide and relatively low concentration of hydrogen; hydrogen having been removed in the first reaction zone. Depending on the quantity of oxygen injection, essentially either all of the carbon monoxide is consumed in the second reaction zone, with some oxygen and little if any carbon monoxide passing downstream of the second reaction zone; or all of the oxygen is consumed in the second reaction zone, with some carbon monoxide and little if any oxygen passing downstream of the second reaction zone.

In yet another and more preferred aspect, a mixture comprised of hydrogen, carbon monoxide and a reactive unsaturated hydrocarbon, or a mixture of one or more of such hydrocarbons is contacted in an initial, or first reaction zone of a series of three reaction zones, with oxygen or an oxygen-containing gas over a catalyst selective for hydrogen oxidation at conditions sufficient to oxidize the hydrogen component of the mixture to form water, while suppressing hydrogenation of the olefinic components of the mixture to obtain effluent which is fed to a second reaction zone of the series. In conducting this series of reactions it is essential to remove the hydrogen first to minimize, avoid, or suppress the hydrogenation reaction between the hydrogen and the reactive unsaturated hydrocarbon, or a mixture of one or more of such hydrocarbons. In the second reaction zone, the effluent is contacted and reacted over an oxidation catalyst capable of oxidizing carbon monoxide in the presence of oxygen at conditions sufficient to oxidize the carbon monoxide component of the mixture to form carbon dioxide. The fact that most carbon-monoxide oxidation catalysts also promote olefin hydrogenation makes it critical to react essentially all or most of the hydrogen in the feed stream prior to its entering the second reaction zone. Suppression of the hydrogenation reaction is enhanced because of the relatively high concentration of carbon monoxide and relatively low concentration of hydrogen; hydrogen having been removed in the first reaction zone. Essentially all of the oxygen, residual or added oxygen, is consumed in the second reaction zone; little if any oxygen passing downstream of the second reaction zone. This may be accomplished by injecting less than stoichiometric quantity of oxygen into the first and/or second reaction zones and allowing a small quantity of carbon monoxide to remain in the effluent of the second reaction zone.

The effluent of the second reaction is fed to a third reaction zone, in which it is contacted and reacted over a catalyst capable of reacting the remaining carbon monoxide with water to form carbon dioxide and hydrogen (i.e., water-gas-shift reaction), and simultaneously consuming the hydrogen produced from the water gas-shift reaction via hydrocarbon hydrogenation. The function of the third reaction zone is to remove essentially the last traces of the unreacted carbon monoxide from the effluent from the second reaction zone and to remove any newly formed hydrogen by contacting the effluent with a bifunctional catalyst for simultaneous water gas-shift reaction and olefin hydrogenation reaction. The concentration of carbon monoxide in the effluent of the second reaction zone, which is fed into the third reaction zone, is preferably controlled and optimized so that (1) there is essentially no oxygen in the effluent of the second reaction zone and (2) the amount of hydrogen generated in the third reaction zone (or the amount of ethylene loss due to hydrogenation in the same zone) is acceptably low. An effluent rich in reactive unsaturated hydrocarbons, denuded of oxygen, hydrogen and carbon monoxide, is recovered from this reaction series. The reaction products, which include water and carbon dioxide, can be readily separated from the hydrocarbon product stream using conventional technology, e.g., a drier, amine treatment, caustic washes or the like.

In conducting the hydrogen oxidation reaction, or first stage reaction whereas the mixture of feed components includes hydrogen, or both hydrogen and carbon monoxide, and the reaction is conducted over a catalyst composed of one or more than one of the metals and/or metal oxides active for hydrogen oxidation but inactive for hydrogenation, and an inert porous support. The metal(s) and/or metal oxide(s) suitable for this purpose include elements selected from Group Ib, IIb, IIIa, IVa, and Va, Suitable inert porous supports include zeolites, carbon, inorganic oxides and mixed oxides including silica, alumina, physically or chemically modified alumina, physically or physically modified silica, aluminosilicate, magnesium oxide, clay, zirconia, titania, porous glass, etc. The active metal(s) could be placed on the porous support using techniques such as impregnation, ion exchange, vapor deposition, mixing, dispersion, etc. The temperature of the reaction is generally in the range of from about 40° C. to about 300° C., and is preferably in the range of from about 50° C. to about 250° C. The flow rate of the entering feed in the gaseous form is in the range of from about 1 GHSV to about 50,000 GHSV, and is preferably in the range of from about 2000 GHSV to about 10,000 GHSV. The pressure maintained in the reaction zone is generally in the range of from about 14.7 psig to about 1,000 psig, and is preferably in the range of from about 14.7 psig to about 500 psig. Depending on process economics and the objective of contaminant removal, the hydrogen concentration in the effluent can be controlled by adjusting the quantity of oxygen injection. The effluent from this reaction zone could contain from less than 1 ppm of hydrogen with some excess oxygen remaining in the stream, to several hundreds ppm of hydrogen with less than 1 ppm oxygen.

In conducting a two-reaction-zone operation for hydrogen and carbon monoxide oxidation reactions, effluent from the first reaction zone, which includes carbon monoxide, reactive unsaturated hydrocarbons and residual hydrogen, if any, is contacted with and reacted in the presence of oxygen, either a residual or added oxygen, over a catalyst composed of one or more than one of the metals and/or metal oxides active for oxidizing carbon monoxide and hydrogen as well as hydrogenation of the hydrocarbon, but inactive for oxidation of the hydrocarbon, and a inert porous support. The metal(s) and/or metal oxides suitable for this purpose include one or more than one of the elements selected from Groups Vb, VIb, VIIb, and VIII. Suitable inert porous supports include zeolites, carbon, inorganic oxides and mixed oxides including silica, alumina, modified alumina, aluminosilicate, magnesium oxide, clay, zirconia, titania, porous glass, etc. The active metal(s) could be placed on the porous support using techniques such as impregnation, ion exchange, vapor deposition, mixing, dispersion, etc. The reaction may be carried out at temperatures in the range of from about 40° C. to about 300° C., and is preferably in the range of from about 50° C. to about 200° C. The effluent from the first reaction zone is introduced into the second reaction zone at flow rate in the range of from about 1 GHSV to about 50,000 GHSV, and is preferably in the range of from about 2000 GHSV to about 10,000 GHSV. The pressure maintained in the second reaction zone is substantially that maintained in the first reaction zone, which generally is in the range of from about 14.7 psig to about 1000 psig, and is preferably in the range of from about 14.7 psig to about 500 psig. Depending on process economics and the objective of contaminant removal, the carbon monoxide concentration in the effluent from the second reaction zone can be controlled by adjusting the quantity of oxygen injection. The effluent from the second reaction zone could contain from less than 1 ppm of carbon monoxide with some excess oxygen remaining in the stream, to 0.1%–0.2% of carbon monoxide with less than 1 ppm of oxygen. At these conditions, there is minimal hydrogenation of the reactive unsaturated hydrocarbons.

In conducting the three-reaction-zone process for hydrogen and carbon monoxide oxidation reactions to produce a product stream essentially denuded of hydrogen, carbon monoxide, and oxygen, the amount of oxygen injection effluent from the second reaction zone, which includes unreacted carbon monoxide, reactive unsaturated hydrocarbons and residual hydrogen, if any, is contacted with and reacted in the presence of water, either from the reaction product of the first reaction zone or added water, over a catalyst composed of one or more than one of the metals and/or metal oxides active for water gas shift reaction and one or more than one of the metals active for hydrogenation of the reactive unsaturated, and an inert porous support. The metal(s) and/or metal oxide(s) suitable for the water gas shift reaction include one or more than one of the elements selected from Groups VIb, VIIb, VIII, and the elements of copper and zinc. Metals suitable for hydrogenation of the reactive unsaturated hydrocarbons include one or more than one of the elements selected from Groups VIb, VIIb, VIII, and the elements of copper and zinc. Suitable inert porous supports include zeolites, carbon, inorganic oxides and mixed oxides including silica, alumina, modified alumina, aluminosilicate, magnesium oxide, clay, zirconia, titania, porous glass, etc. The active metal(s) may be placed on the porous support using techniques such as impregnation, ion exchange, vapor deposition, mixing, dispersion, etc. The reaction may be carried out at temperatures in the range of from about 100° C. to about 500° C., and preferably in the range of from about 150° C. to about 250° C. Effluent from the second reaction zone is introduced into the third reaction zone at flow rate in the range of from about 1 GHSV to about 50,000 GHSV, and is preferably in the range of from about 2000 GHSV to about 10,000 GHSV. The pressure maintained in the third reaction zone is substantially the same as that maintained in the first and second reaction zones, generally in the range of from about 14.7 psig to about 1000 psig, and preferably in the range of from about 14.7 psig to about 500 psig. At these conditions, essentially all of the carbon monoxide in the zone is reacted with water to produce carbon dioxide and hydrogen, and essentially all the resulting hydrogen is consumed by hydrogenation of reactive unsaturated hydrocarbon which takes place in the same reaction zone and produces saturated or paraffinic hydrocarbons. In this way, hydrogen and carbon monoxide can be essentially completely purged from the system with minimal loss of the reactive unsaturated hydrocarbon product. Since the quantity of carbon monoxide fed to the third reaction zone is controlled at acceptably low levels, the quantity of hydrogen generated and consequently the amount of ethylene loss via hydrogenation would not be sufficient to jeopardize the economics.

In conducting the one-reaction-zone process for hydrogen oxidation reaction, oxygen is introduced into the reaction zones in concentration in the range of from about 50 mole % to about 500 mole %, and is preferably in the range of from about 95 mole % to about 150 mole %, based on the considerations of (1) the amount of oxygen required to react stoichiometrically with the hydrogen present in the reaction zone, and (2) process economics. At these reaction conditions, the hydrogen substantially completely react with this amount of oxygen, while simultaneously avoiding or suppressing hydrogenation and oxidation of the reactive unsaturated hydrocarbon. The total of the oxygen or oxygen-containing gas required for these reactions can be introduced into the reaction zone, via one or a plurality of oxygen injection points located within the reaction zone. The effluent from the reaction zone will contain essentially minimal amounts of hydrogen.

The conditions of operation in the reaction zone is thus sufficient to reduce the concentration of hydrogen to levels below about 500 wppm, and preferably in the range of below about 1 wppm. The amount of oxygen in the effluent from the reaction zone may range from 1 wppm up to 1000 wppm. Minimal amounts of the reactive unsaturated hydrocarbons are hydrogenated in the two zones, loss of reactive unsaturated hydrocarbons within these zones generally not exceeding about 0.2% by volume based on the reactive unsaturated hydrocarbons in the feed to the first reaction zone; and preferably does not exceed about 00.05% by volume. Thus, generally at least about 95.0 volume %, or from about 95.0 volume % to greater than 99.9 volume %, preferably from about 99.5 volume % to greater than 99.9 volume % of the reactive unsaturates of the feed to the first reaction zone are recovered. If desirable, the oxygen remaining in the effluent can be removed using oxygen scavengers commonly known to those skilled in the art such as reduced metals. The reaction products, which is essentially water, can be readily separated from the olefinic hydrocarbons using conventional technology, e.g., a drier or the like.

In conducting the two-reaction-zone process for hydrogen oxidation-carbon monoxide oxidation reactions oxygen is introduced into the reaction zones in concentration in the range of from about 50 mole % to about 500 mole %, and is preferably in the range of from about 95 mole % to about 150 mole %, based on the amount of oxygen required to react stoichiometrically with the hydrogen and carbon monoxide present in the first two reaction zones. At these reaction conditions, the hydrogen and carbon monoxide substantially completely react with this amount of oxygen, while simultaneously avoiding or suppressing hydrogenation and oxidation of the reactive unsaturated hydrocarbons. The total of the oxygen or oxygen-containing gas required for these reactions can be introduced into the first reaction zone, the oxygen needed in the second reaction zone for oxidation of the carbon monoxide being transported thereto via unreacted oxygen in the effluent from the first zone, or the oxygen can be supplied directly to the two stages via one or a plurality of oxygen injection points located within the first or both the first and second of the reaction zones. The effluent from the second reaction zone will contain essentially minimal amounts of hydrogen and carbon monoxide. The conditions of operation in each of the two reaction zones is thus sufficient to reduce the concentration of hydrogen to levels below about 500 wppm, preferably below about 1 wppm; and the concentration of carbon monoxide to levels below 2000 wppm, preferably below 1 wppm. The amount of oxygen in the effluent from the second reaction zone could range from 1 ppm up to 1000 ppm. Minimal amounts of the reactive unsaturated hydrocarbons are hydrogenated in the two zones, loss of reactive unsaturated hydrocarbons within these zones generally not exceeding about 0.2% by volume based on the reactive unsaturates in the feed to the first reaction zone; and preferably does not exceed about 0.1% by volume. Thus, generally at least about 95.0 volume %, or from about 95.0 volume % to about 99.9 volume %, preferably from about 99.5 volume % to about 99.9 volume % of the reactive unsaturates of the feed to the first reaction zone are recovered. If desirable, the oxygen remaining in the effluent can be removed using oxygen scavengers commonly known to those skilled in the art such as reduced metals. The reaction products, which include water and carbon dioxide, can be readily separated from the olefinic hydrocarbons using conventional technology, e.g., a drier, amine treatment, caustic washes or the like.

In conducting the three-reaction-zone process for the purpose of producing an olefinic stream that is completely denuded of oxygen, hydrogen, and carbon monoxide via hydrogen and carbon monoxide oxidation reactions, oxygen is introduced into the reaction zones in concentration in the range of from about 50 mole % to about 100 mole %, preferably in the range of from about 90 mole % to about 99 mole %, based on the amount of oxygen required to react stoichiometrically with the hydrogen and carbon monoxide present in the first two reaction zones. At these reaction conditions, this amount of oxygen reacts with substantially all of hydrogen and most of carbon monoxide, while simultaneously avoiding or suppressing hydrogenation and oxidation of the reactive unsaturate. The amount of oxygen in the effluent from the second reaction zone generally does not exceed about 100 wppm, and preferably does not exceed about 1 wppm. The total of the oxygen or oxygen-containing gas required for these reactions can be introduced into the first reaction zone, the oxygen needed in the second reaction zone for oxidation of the carbon monoxide being transported thereto via unreacted oxygen in the effluent from the first zone, or the oxygen can be supplied directly to the two stages via one or a plurality of oxygen injection points located within the first or both the first and second of the reaction zones. The effluent from the second reaction zone will contain essentially no hydrogen and a control amount of unreacted carbon monoxide. The conditions of operation in each of the three reaction zones is thus sufficient to reduce the concentration of hydrogen to levels below about 100 wppm, preferably below about 1 wppm; and the concentration of carbon monoxide to levels below 0.2% by volume, and preferably below 0.1% by volume. Minimal amounts of the reactive unsaturated hydrocarbons are hydrogenated in the three zones, loss of reactive unsaturated hydrocarbons within these zones generally not exceeding about 0.2% by volume based on the olefins in the feed to the first reaction zone; and preferably does not exceed about 0.1% by volume. Thus, generally at least about 95.0 volume %, or from about 95.0 volume % to about 99.9 volume %, preferably from about 99.5 volume % to about 99.9 volume % of the reactive unsaturated hydrocarbons in the feed to the first reaction zone are recovered. It is not necessary to remove the oxidation products of hydrogen and carbon monoxide, e.g., water and carbon dioxide, from the effluent of the second reaction zone. As high water concentration would facilitate the shift gas reaction in the third reaction zone. If desirable, the reaction products can be readily separated from the reactive unsaturated hydrocarbon product stream after the third reaction zone using conventional technology, e.g., a drier, amine treatment, caustic washes or the like.

Catalysts suitable for the first reaction zone constitute of a composite inclusive of one or more than one of the metals or metal oxides selected from Groups Ib, IIb, IIIa, IVa, and Va with the metal silver being preferred and inert porous supports, if desired, include zeolites, carbon, inorganic oxides and mixed oxides including silica, alumina, physically or chemically modified alumina, physically or physically modified silica, aluminosilicate, magnesium oxide, clay, zirconia, titania, porous glass, etc. A preferred catalyst is a bulk silver catalyst or silver composited with a refract of inorganic oxide support. The metals or metal oxides are chosen for their low activity or inactive nature for reactions of the reactive unsaturates including particularly hydrogenation, as well as oligomerization, oxidation, alkylation, or other chemical reaction at the conditions of operation. The metal(s), and/or metal oxide(s), may be placed on the porous support using techniques such as impregnation, ion exchange, vapor deposition, mixing, dispersion, or the like. The concentration of the metal(s) and/or metal oxide(s) is generally in the range from about 0.01 wt. % to about 75 wt. %, and is preferably in the range of from about 0.2 wt. % to about 5 wt. %, based on the weight of total catalyst (dry basis).

Catalysts suitable for the second reaction zone constitute of a composite inclusive of one or more than one of the metals or metal oxides selected from Groups Vb, VIb, VIIb, and VIII and inert porous supports include zeolites, carbon, inorganic oxides and mixed oxides including silica, alumina, physically or chemically modified alumina, physically or physically modified silica, aluminosilicate, magnesium oxide, clay, zirconia, titania, porous glass, etc. The metals or metal oxides are chosen for their low activity or inactive nature for olefin reactions including oligomerization, oxidation, alkylation, or other chemical reaction at the conditions of operation. The metal(s), and/or metal oxide(s), may be placed on the porous support using techniques such as impregnation, ion exchange, vapor deposition, mixing, dispersion, or the like. The concentration of the metal(s) and/or metal oxide(s) is generally in the range of from about 0.01 wt. % to about 50 wt. %, and is preferably in the range of from about 0.2 wt. % to about 5 wt. %, based on the weight of total catalyst (dry basis).

Catalysts suitable for the third reaction zone constitute of a composite inclusive of one or more than one of the metals or metal oxides selected from Groups VIb, VIIb, and VIII and the elements of copper and zinc, and inert porous supports include zeolites, carbon, inorganic oxides and mixed oxides including silica, alumina, physically or chemically modified alumina, physically or physically modified silica, aluminosilicate, magnesium oxide, clay, zirconia, titania, porous glass, etc. The metals or metal oxides are chosen for their low activity or inactive nature for olefin reactions including oligomerization, oxidation, alkylation, or other chemical reaction at the conditions of operation. The metal(s), and/or metal oxide(s), may be placed on the porous support using techniques such as impregnation, ion exchange, vapor deposition, mixing, dispersion, or the like. The concentration of the metal(s) and/or metal oxide(s) is generally in the range of from about 0.01 wt. % to about 100 wt. %, and is preferably in the range of from about 1.0 wt. % to about 50 wt. %, based on the weight of total catalyst (dry basis).

The following examples are illustrative of the more salient features of the invention. All temperatures are given in terms of degrees Centigrade, and parts and percentages are given in terms of weight except as otherwise specified.

EXAMPLE 1

In this Example, hydrogen is removed from a 2 component mixture of hydrogen and ethylene, by selective oxidation of the hydrogen over a silver catalyst, without the undesired side effect of hydrogenation of the ethylene. A gaseous feed constituted of a mixture of 56 wppm oxygen, 1040 wppm carbon monoxide, 5.0 vol. % hydrogen and 94.9 vol. % ethylene was contacted and reacted over a 2 wt. % Ag-on-$Al_2O_3$ catalyst (TOR-20X, by Enichem Co., Japan) at 80° C., 325 psig, and 5000 GHSV. The catalyst was employed without reduction. The composition of the feed and products of the reaction are summarized.

TABLE 1

|         | $O_2$, wppm | CO, wppm | $CO_2$, wppm | $H_2O$, wppm | Ethane, wppm |
|---------|-------------|----------|--------------|--------------|--------------|
| Feed    | 56          | 1040     | 5            | 5            | 130          |
| Product | <1          | 1035     | 9            | 120          | 130          |

These data thus show that the principal reaction was between hydrogen and oxygen to form water. Essentially no ethylene was hydrogenated during the reaction; no ethane formation having been detected.

EXAMPLE 2

This Example illustrates the selective oxidation of carbon monoxide; i.e., the formation of carbon dioxide from carbon monoxide, using a multi-component mixture with minimal hydrogenation of ethylene. A 0.6 wt. % platinum-on-alumina catalyst was loaded into a reactor and reduced under hydrogen at 350° C. prior to use. A feed mixture constituted of 420 ppm oxygen, 962 wppm carbon monoxide, 20 ppm $CO_2$, 5.7 vol. % hydrogen, 77.2 vol. % ethylene, 17.1 vol. % propylene, 0.4 vol. % butene-1, 140 ppm methane, 140 ppm ethane, and 350 ppm propane was passed over the catalyst and reacted at the conditions of 73° C., 24 psig, and a flow rate of approximately 5000 GHSV. Olefin hydrogenation was monitored by measuring the concentration of ethane in feed and product using GC. CO and $CO_2$ concentrations in feed and product were used to measure CO oxidation. $H_2$ oxidation was monitored by measuring the water content in feed and product. Oxygen concentration was analyzed using an oxygen analyzer manufactured by Teledyne Analytical Instruments, Inc. Results are listed below:

TABLE 2

|         | $O_2$, wppm | CO, wppm | $CO_2$, wppm | $H_2O$, wppm | Ethane, wppm |
|---------|-------------|----------|--------------|--------------|--------------|
| Feed    | 420         | 962      | 20           | <1           | 140          |
| Product | 200         | 410      | 530          | 20           | 630          |

The test indicates Pt-based catalysts' oxidation selectivity toward CO over $H_2$ and ethylene. Furthermore, ethylene hydrogenation was maintained at a fairly low level of about 500 ppm. Thus, CO can be selectively removed via oxidation to form $CO_2$. The separation performance can be readily further improved through catalyst and process optimization.

EXAMPLE 3

This Example illustrates the selective removal of hydrogen and carbon monoxide from an olefin stream by oxidation of both the hydrogen and carbon monoxide using a staged reactor system. Three reactors were employed in series: a first reactor which contained the same silver catalyst as in Example 1, except that the catalyst was reduced under hydrogen at 250° C. for 16 hours prior to use; a second reactor which contained a catalyst constituted of 2.8 wt. % platinum on a 3A molecular sieve, prereduced at 350° C. for 3 hours prior to use; and a third reactor which contained a commercial low temperature shift gas catalyst (Katalco 53-1, 1/3 CuO+1/3 ZnO+1/3 $Al_2O_3$) which had been prereduced at 220° C. under hydrogen for a 24 hour period.

A feed was prepared by mixing a hydrocarbon stream of 94.342% ethylene, 5.294% $H_2$, 0.342% CO, and 0.022% ethane with an oxygen-containing stream (90% nitrogen+ 10% oxygen). After the mixing, the feed had a composition of 71.455% ethylene, 22.137% nitrogen, 4.010% $H_2$, 2.123% $O_2$, 0.259% CO, and 0.017% ethane.

The feed was introduced into the first reactor with the effluent from the first reactor flowing as feed to the second reactor of the series, and the effluent from the second reactor flowing as feed to the third reactor of the series. The first reactor was operated at 176° C., 20 psig, and 2000 GHSV, conditions under which hydrogen was selectively oxidized to water. The second reactor was operated at 104° C., 20 psig, and 2000 GHSV, conditions at which carbon monoxide was oxidized to carbon dioxide. In the third reactor, which was operated at 201° C., 20 psig, and 2000 GHSV, residual carbon monoxide was reacted with water to carbon dioxide and hydrogen. The resulting hydrogen was eliminated in situ via a secondary hydrogenation reaction with ethylene. These results are summarized in Table 3.

TABLE 3

|  | Feed | Effluent Feed from First Reactor | Effluent Feed from Second Reactor | Effluent Feed from Third Reactor |
|---|---|---|---|---|
| Ethylene, Volume % | 71.455 | 76.848 | 77.405 | 77.265 |
| $N_2$, Volume % | 22.137 | 22.795 | 22.250 | 22.359 |
| $H_2$, Volume % | 4.010 | 0.029 | 0.029 | 4 ppm |
| $O_2$, Volume % | 2.123 | 0.065[1] | 25 ppm[1] | 1 ppm[1] |
| CO, Volume % | 0.259 | 0.246 | 0.116 | 80 ppm |
| Ethane, Volume % | 0.017 | 0.029 | 0.045 | 0.102 |
| $CO_2$, Volume % | NA | 0.053 | 0.154 | 0.266 |

[1]Note: These oxygen levels were analyzed using oxygen analyzer. All other analyses were carried out with GC's.

As illustrated by these examples, one can see how the hydrogen and oxygen levels across the first reactor are reduced without the undesirable effect of hydrogenating the ethylene.

In the second reactor, the level of carbon monoxide is reduced and the residual oxygen is consumed. In the third reactor, the level of oxygen is even further reduced.

One can see the benefits of this invention enable one to selectively separate hydrogen and carbon monoxide from a reactive unsaturate without significant loss of the reactive unsaturate via undesirable side reactions.

We claim:

1. A process for removing hydrogen from a mixture which includes hydrogen and unsaturated hydrocarbons which comprises (a) contacting said mixture with oxygen or an oxygen-containing gas over a catalyst comprising one or more than one of the metals or metal oxides selected from the elements of Groups Ib, IIb, IIIa, IVa and Va of the Periodic Table of Elements at reaction conditions sufficient to oxidize the hydrogen component of the mixture to form water while suppressing hydrogenation of the unsaturated hydrocarbons of the mixture, wherein the amount of oxygen present is in the range of from greater than about 100 mole % to about 500 mole % of the stoichiometric amount of oxygen required to react with the hydrogen, and (b) recovering an effluent rich in unsaturated hydrocarbons therefrom which contains less than 500 wppm hydrogen.

2. The process of claim 1 wherein the temperature of the reaction ranges from about 40° C. to about 300° C., the pressure of the reaction ranges from about 14.7 psig to 1000 psig, and the flow rate of the entering feed ranges from about 1 GHSV to about 50,000 GHSV.

3. The process of claim 2 wherein the temperature of the reaction ranges from about 50° C. to about 250° C., the pressure of the reaction ranges from about 14.7 psig to 500 psig, and the flow rate of the entering feed ranges from about 2000 GHSV to about 10,000 GHSV.

4. The process of claim 1 wherein oxygen is supplied to the hydrogen in the mixture in an amount in the range of from twice more than stoichiometric to greater than stoichiometric of the amount of oxygen required for complete reaction with the hydrogen.

5. The process of claim 4 wherein the amount of oxygen present is in the range of from greater than 100 mole % to about 150 mole % of the stoichiometric amount of oxygen required to react with the hydrogen.

6. The process of claim 1 wherein the catalyst comprises an inert porous support selected from carbon, inorganic oxides, and mixtures thereof.

7. The process of claim 1 wherein the feed mixture is comprised of hydrogen, and unsaturated hydrocarbons, and the effluent of the reaction is comprised of less than 1 ppm hydrogen.

8. A process for removing hydrogen and carbon monoxide from a mixture which includes hydrogen, carbon monoxide, and unsaturated hydrocarbons which comprises (a) contacting said mixture in a first reaction zone, with oxygen or an oxygen-containing gas in such an amount that the amount of oxygen present is in the range of from greater than about 100 mole percent to about 500 mole percent of the stoichiometric amount of oxygen required to react with the hydrogen over a catalyst comprising one or more than one of the metals or metal oxides selected from the elements of Groups Ib, IIb, IIIa, IVa and Va of the Periodic Table of Elements at reaction conditions sufficient to oxidize the hydrogen component of the mixture to form water while suppressing hydrogenation of the unsaturated hydrocarbons of the mixture, and removing therefrom an effluent which contains less than 500 wppm hydrogen, (b) contacting said effluent, in a second reaction zone, over an oxidation catalyst, in the presence of oxygen or an oxygen-containing gas at conditions sufficient to oxidize the carbon monoxide component of the mixture to form carbon dioxide, and (c) recovering from said second reaction zone an effluent rich in unsaturated hydrocarbons and denuded of hydrogen and carbon monoxide.

9. The process of claim 8 wherein in said first reaction zone the temperature of the reaction ranges from about 40° C. to about 300° C. and the flow rate of the entering feed ranges from about 1 GHSV to about 50,000 GHSV, and in said second reaction zone the temperature of the reaction ranges from about 40° C. to about 300° C., and the flow rate that the effluent is introduced into said second reaction zone ranges from about 1 GHSV to about 50,000 GHSV.

10. The process of claim 9 wherein in said first reaction zone the temperature of the reaction ranges from about 50° C. to about 250° C. and the flow rate of the entering feed ranges from about 2000 GHSV to about 10,000 GHSV, and in said second reaction zone the temperature of the reaction ranges from about 50° C. to about 200° C. and the flow rate of the entering feed ranges from about 2000 GHSV to about 10,000 GHSV.

11. The process of claim 8 wherein the amount of oxygen added to said reaction zones ranges from greater than about 100% to about 150% based on the total amount of oxygen that will react with the hydrogen and carbon monoxide present in said zones.

12. The process of claim 8 wherein the catalyst of said first reaction zone comprises silver.

13. The process of claim 8 wherein the catalyst of said first reaction zone comprises an inert porous support selected from carbon, inorganic oxides, and mixtures thereof.

14. The process of claim 13 wherein the catalyst of said first reaction zone comprises a zeolite.

15. The process of claim 8 wherein the catalyst of said second reaction zone comprises one or more than one of the metals and/or metal oxides selected from the elements of Group Vb, VIb, VIIb and VIII of the Periodic Table of Elements.

16. The process of claim 15 wherein the catalyst of said second reaction zone is a Group VIII noble metal.

17. The process of claim 8, wherein the catalyst of said second reaction zone comprises an inert porous support selected from carbon, inorganic oxides, and mixtures thereof.

18. A process for removing hydrogen and carbon monoxide from a mixture which includes hydrogen, carbon monoxide, and unsaturated hydrocarbons which comprises (a) contacting said mixture in a first reaction zone, with oxygen or an oxygen-containing gas in such an amount that the amount of oxygen present is in the range of from greater than about 100 mole percent to about 500 mole percent of the stoichiometric amount of oxygen required to react with the hydrogen over a catalyst comprising one or more than one of the metals or metal oxides selected from the elements of Groups Ib, IIb, IIIa, IVa and Va of the Periodic Table of Elements at conditions sufficient to oxidize the hydrogen component of the mixture to form water while suppressing hydrogenation of the unsaturated hydrocarbons of the mixture and removing therefrom an effluent which contains less than 500 wppm hydrogen, (b) contacting said effluent, in a second reaction zone, over an oxidation catalyst, in the presence of oxygen or an oxygen-containing gas at conditions sufficient to oxidize the carbon monoxide component of the mixture to form carbon dioxide and removing therefrom an effluent, (c) contacting said effluent, in a third reaction zone, over a bifunctional catalyst at conditions sufficient to react carbon monoxide with water to form carbon dioxide and hydrogen, and reacting the resulting hydrogen with olefin, and removing therefrom an effluent, and (d) recovering from said third reaction zone an effluent which is rich in unsaturated hydrocarbons and denuded of hydrogen, carbon monoxide, and oxygen.

19. The process of claim 18 wherein the catalyst in the third reaction zone is comprised of a Cu—ZnO mixture, and the reaction is conducted at temperature in the range of from about 40° C. to about 300° C., and the flow rate of the entering feed ranges from about 1 GHSV to about 20,000 GHSV.

* * * * *